United States Patent
Lei

(10) Patent No.: US 9,321,804 B2
(45) Date of Patent: Apr. 26, 2016

(54) SYNTHESIS AND USE OF ANTI-TUMOR DRUG LQC-Y

(71) Applicant: Beijing University of Chinese Medicine, Beijing (CN)

(72) Inventor: Haimin Lei, Beijing (CN)

(73) Assignee: 3D MEDICINES, LTD., Beijing (CN)

( * ) Notice: Subject to any disclaimer, the term of this patent is extended or adjusted under 35 U.S.C. 154(b) by 185 days.

(21) Appl. No.: 14/017,857

(22) Filed: Sep. 4, 2013

(65) Prior Publication Data

US 2014/0011786 A1 Jan. 9, 2014

Related U.S. Application Data

(63) Continuation of application No. PCT/CN2011/081530, filed on Oct. 28, 2011.

(30) Foreign Application Priority Data

Mar. 9, 2011 (CN) .......................... 2011 1 0055102

(51) Int. Cl.
*C07J 43/00* (2006.01)
*C07D 241/12* (2006.01)
*C07D 405/14* (2006.01)
*C07J 63/00* (2006.01)

(52) U.S. Cl.
CPC ............. *C07J 43/003* (2013.01); *C07D 241/12* (2013.01); *C07D 405/14* (2013.01); *C07J 63/008* (2013.01)

(58) Field of Classification Search
CPC ...................................................... C07J 63/008
USPC .......................................... 540/113; 544/336
See application file for complete search history.

(56) References Cited

PUBLICATIONS

Ribatti et al., "The Chick Embryo Chorioallantoic Membrane as a Model for in vivo Research on Anti-Angiogenesis," *Current Pharmaceutical Biotechnology*, vol. 1, No. 1, pp. 73-82 (2000).
Folkman, "What Is the Evidence that Tumors Are Angiogenesis Dependent?," *Journal of the National Cancer Institute*, vol. 82, No. 1, pp. 4-7, Jan. 3, 1990.
Greten et al., "Molecular therapy for the treatment of hepatocellular carcinoma," *British Journal of Cancer*, vol. 100, pp. 19-23 (2009).

*Primary Examiner* — Barbara P Badio
(74) *Attorney, Agent, or Firm* — Nath, Goldberg & Meyer; Tanya E. Harkins

(57) ABSTRACT

Disclosed are the general structural formula of LQC-Y as well as the synthesis and use thereof. Pharmacological experiments demonstrated the marked antitumor effect of such compounds. Single day administration of LQC-Y3 to mice at a maximum dose of 6000 mg/kg showed no toxicity response during the 14-day continuous observation period, indicating the high safety of the compounds, and the compounds can be used to prepare medicaments for preventing and treating carcinomas such as liver cancer, lung cancer. In the general structural formula of LQC-Y, R represents steroid compounds such as cholic acid, deoxycholic acid, ursodeoxycholic acid, chenodeoxycholic acid, and hyodeoxycholic acid and so on; triterpenoid compounds such as oleanolic acid, ursolic acid, pachymic acid, glycyrrhetinic acid and glycosides thereof and so on; emodic acid, emodin and other mono-substituted or poly-substituted structures of anthraquinone parent nucleus; baicalein, baicalin and other flavonoid; shikimic acid, mono-substituted shikimic acid or poly-substituted shikimic acid; gardenia acid and other iridoid acid derivatives; paeonol, curcumin and structural derivatives thereof.

10 Claims, No Drawings

SYNTHESIS AND USE OF ANTI-TUMOR DRUG LQC-Y

CROSS REFERENCE

This is a continuation application of PCT/CN2011/081530 filed Oct. 28, 2011, which claims priority to Chinese Patent Application No. CN201110055102.X filed Mar. 9, 2011, each of which is herein incorporated by reference.

TECHNICAL FIELD

The present invention relates to chemistry and bioscience filed, and specifically relates to LQC-Y general structural formula and the synthesis and the use thereof. It is proved by pharmacological experiments that this kind of compounds have a notable anti-tumor effect. No toxic reaction is observed in 14 days by continuous observation when a maximum dosage of 6000 mg/kg LQC-Y3 per day is administrated to mice, which indicates that this medicine is of high safety and can be used to prepare a medicine for preventing and treating the tumor diseases such as liver cancer, lung cancer and immune diseases.

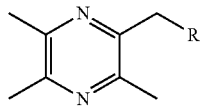

LQC-Y general structural formula

Wherein R represents a steroid, such as cholic acid, deoxycholic acid, ursodesoxycholic acid, chenodeoxycholic acid, hyodeoxycholic acid, etc.; triterpene, such as oleanolic acid, ursolic acid, pachymic acid, glycyrrhetinic acid, etc.; emodic acid, emodin and other monosubstituted or multisubstituted structure of anthraquinone parent nucleus; baicalein, baicalin and other flavonoid; shikimic acid, monosubstituted or multisubstituted shikimic acid; gardenia acid and other iridoid acid derivative; paeonol, curcumin and the structural derivative thereof.

BACKGROUND ART

Tumor is one of main diseases that are threatening the human health and ranks top 2 in terms of the mortality rate of the diseases. It has been proved by a plenty of clinical treatments that the chemotherapy and the radiotherapy will damage the normal cells greatly when killing the tumor cells. These therapies cause severe damage to the hemopoietic system and the immunologic function of the human body and result in the death of the patients easily. The dependence on the vessels is common for all the tumor cells and the angiogenesis is a very important step of tumor growth and tumor metastasis. No matter whether it is a primary tumor or a secondary tumor, once it grows into a diameter of more than 2 mm, angiogenesis will take place therein, followed by rapid growth and metastasis of the tumor. (Folkman J. what is the evidence that tumors are angiogenesis department? J Natl Cancer Inst. 1990, 82:4-6.)

There are three main types of medicines used for treating tumor at present, namely cytotoxic drug, auxiliary drug for the chemotherapy and the radiotherapy, and angiogenesis inhibitor. The angiogenesis inhibitor is a very promising anti-tumor medicine at present.

The present invention screens out a type of compound which is novel in structural skeleton with definite activity, safe and low toxicity from more than 100 different structural modifications of natural product based on CAM model (Ribatti D, Vacca A, et al. The chick embryo chorioallantoic membrane as a model for in vivo research on anti-angiogenesis. Curr Pharm Biotechnol. 2000 July; 1(1): 73-82) and VEGF (Gretten T F, Korangy F, et al. Molecular therapy for the treatment of hepatocellular carcinoma. Br J Cancer. 2009 Jan. 13; 100 (1): 19-23) screening and names it LQC-Y.

SUMMARY OF THE INVENTION

The first aim of the present invention is to provide compounds of the general structural formula (formula 1) of LQC-Y.

The second aim of the present invention is to provide a synthesis route of LQC-Y.

The third aim of the present invention is to provide a use of LQC-Y in anti-tumor field.

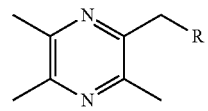

formula 1

Formula 1 is the general structural formula of LQC-Y, wherein R represents a steroid, such as cholic acid, deoxycholic acid, ursodesoxycholic acid, chenodeoxycholic acid, hyodeoxycholic acid, etc.; triterpene, such as oleanolic acid, ursolic acid, pachymic acid, glycyrrhetinic acid, etc.; emodic acid, emodin and other monosubstituted or multisubstituted structure of anthraquinone parent nucleus; baicalein, baicalin and other flavonoid; shikimic acid, monosubstituted shikimic acid or multisubstituted shikimic acid; gardenia acid and other iridoid acid derivative; paeonol, curcumin and the structural derivative thereof. The aims of the present invention can be achieved by the following means.

A method for synthesizing the LQC-Y, comprising the following steps:

(1) dissolving cholic acid into an organic solvent to react with bromotetramethylpyrazine in the presence of a catalyst at a certain temperature to generate LQC-Y1 (compound 1: LQC-Y1);

(2) dissolving deoxycholic acid into an organic solvent to react with bromotetramethylpyrazine in the presence of a catalyst at a certain temperature to generate LQC-Y2 (compound 2: LQC-Y2);

(3) dissolving oleanolic acid into an organic solvent to react with bromotetramethylpyrazine in the presence of a catalyst at a certain temperature to generate LQC-Y3 (compound 3: LQC-Y3);

(4) dissolving glycyrrhetinic acid into an organic solvent to react with bromotetramethylpyrazine in the presence of a catalyst at a certain temperature to generate LQC-Y4 (compound 4: LQC-Y4);

(5) dissolving pachymic acid into an organic solvent to react with bromotetramethylpyrazine in the presence of a catalyst at a certain temperature to generate LQC-Y5 (compound 5: LQC-Y5);

(6) dissolving emodic acid into an organic solvent to react with bromotetramethylpyrazine in the presence of a catalyst at a certain temperature to generate LQC-Y6 (compound 6: LQC-Y6);

(7) dissolving emodin into an organic solvent to react with bromotetramethylpyrazine in the presence of a catalyst at a certain temperature to generate LQC-Y7 (compound 7: LQC-Y7);

(8) dissolving curcumin into an organic solvent to react with bromotetramethylpyrazine in the presence of a catalyst at a certain temperature to generate LQC-Y8 (compound 8: LQC-Y8);

(9) dissolving paeonol into an organic solvent to react with bromotetramethylpyrazine in the presence of a catalyst at a certain temperature to generate LQC-Y9 (compound 9: LQC-Y9);

(10) dissolving shikimic acid into an organic solvent to react with bromotetramethylpyrazine in the presence of a catalyst at a certain temperature to generate LQC-Y10 (compound 10: LQC-Y10);

(11) dissolving baicalein into an organic solvent to react with bromotetramethylpyrazine in the presence of a catalyst at a certain temperature to generate LQC-Y11 (compound 11: LQC-Y11);

the reaction formulas of step (1), (2), (3), (4), (5), (6), (7), (8), (9), (10) and (11) of the above method are as follows:

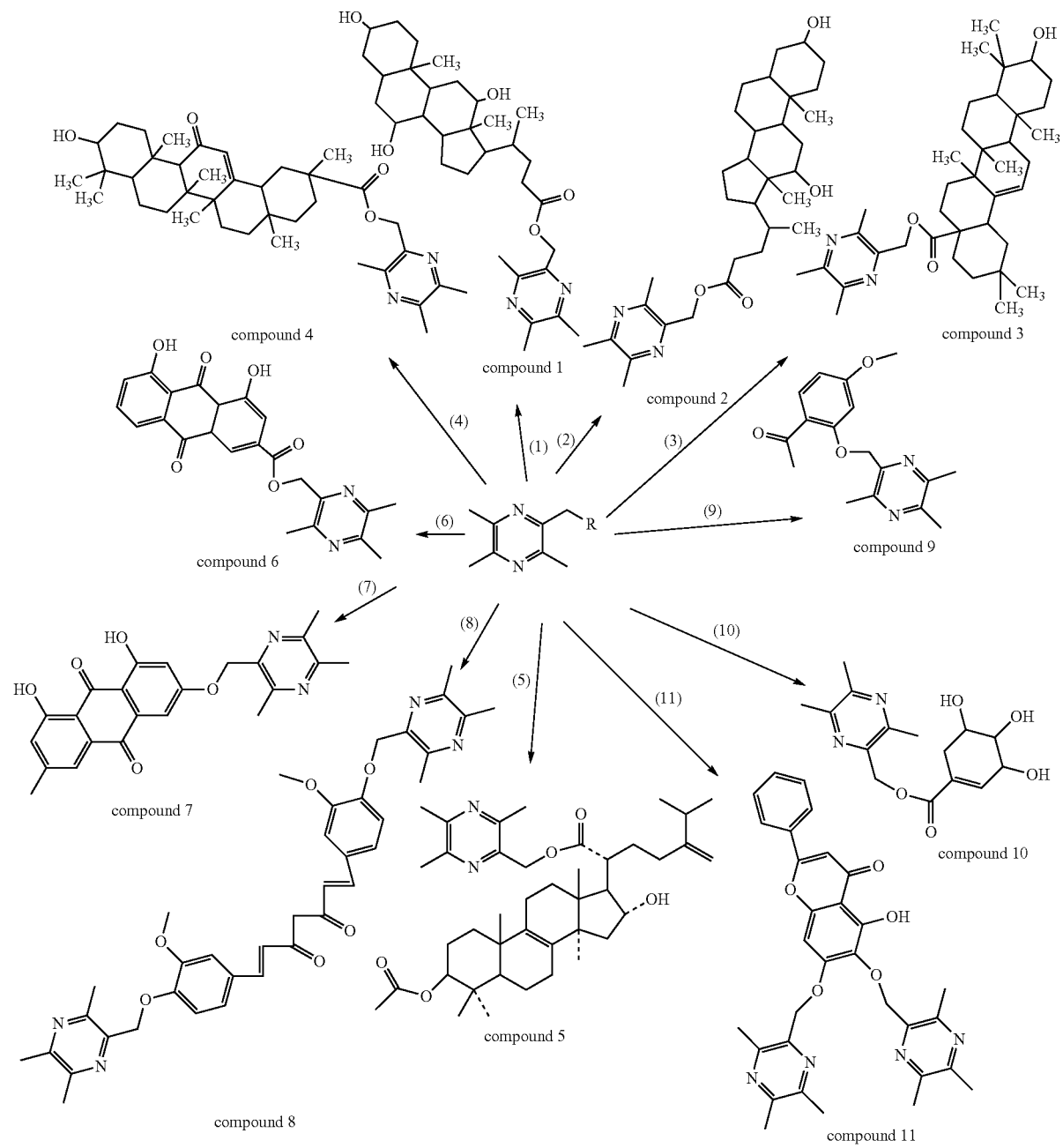

(1) In said method for synthesizing LQC-Y, the organic solvent used is ether, alcohol, alkane, aromatic hydrocarbon, ketone, halogenated alkane, amide, nitrile and ester having 1-20 carbon atoms or mixture thereof at all kinds of ratios; the temperature is −20° C. to 250° C.; the catalyst is inorganic alkali or organic alkali, wherein a representative of the inorganic alkali is kalium carbonate and a representative of the organic alkali is triethylamine; the reaction system needs inert gas protection.

(2) In said method for synthesizing LQC-Y, wherein LQC-Y8 and LQC-Y11 are prepared and the mole ratios of curcumin to bromotetramethylpyrazine and baicalin to bromotetramethylpyrazine are 1:2-10;

(3) the synthesized LQC-Y (1-11) has evident activity of inhibiting tumor angiogenesis;

(4) the synthesized LQC-Y2 and 3 (compound 2 and 3) can inhibit the growth of S180 tumor effectively and increase the spleen index of mice;

(5) when the synthesized LQC-Y3 (compound 3) is administrated at a maximum dosage of 6.0 g/kg per day to a mouse, no toxic or side effect is observed in 14 days, and (6) the synthesized LQC-Y can be prepared into an oral formulation, an injection or an external formulation used in treating and preventing tumor.

A ester of R-acid with trimethyl pyrazine methanol represented by formula 1 and the pharmaceutically acceptable salt thereof: wherein the R-acid is selected from cholic acid, deoxycholic acid, oleanolic acid, glycyrrhetinic acid, pachymic acid, emodic acid or shikimic acid;

An ether of R-phenol with trimethyl pyrazine methanol represented by formula 1 and the pharmaceutically acceptable salt thereof: wherein R-phenol is selected from chrysophanol or paeonol.

A compound of formula 2:

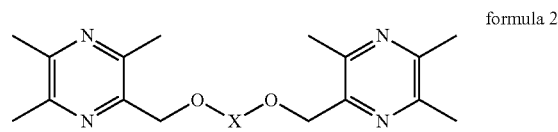

formula 2

Wherein X is selected from (1E,6E)-1,7-heptyl-1,6-diene-3,5-diketone (the obtained compound is as formula 3) or 5-hydroxy-2-phenyl-4H-benzopyran-4-one-6,7-(the obtained compound is as formula 4).

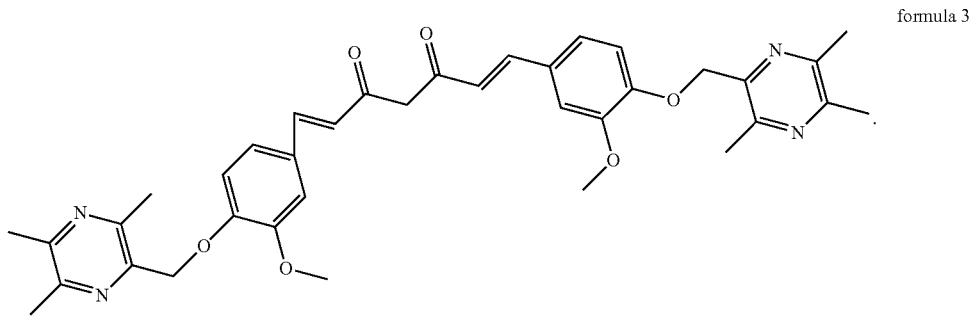

formula 3

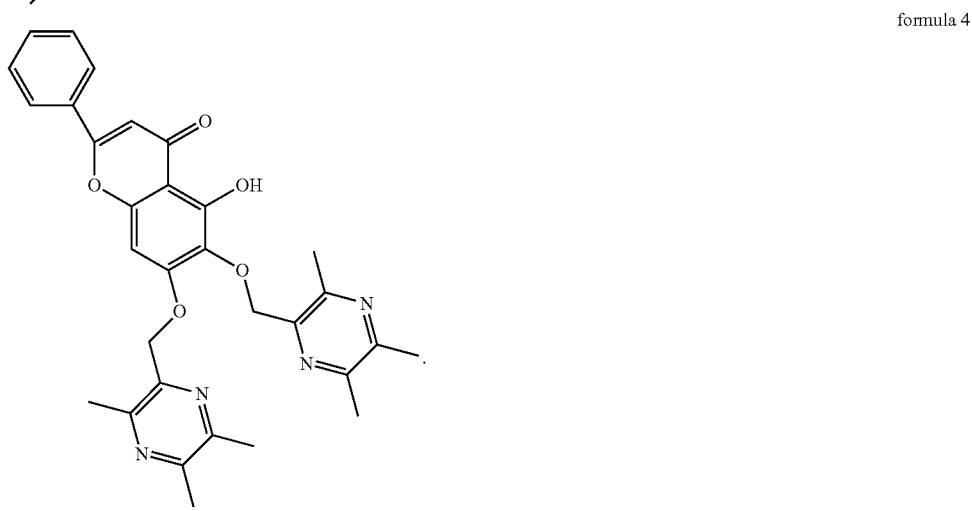

formula 4

The compound of formula 1 and the pharmaceutically acceptable salt thereof:
wherein R is selected from an ester which is substituted by a substituted cyclopentanoperhydrophenanthrene, a phenol which is substituted by a substituted cyclopentanoperhydrophenanthrene, a substituted flavonoid phenol, a substituted iridoid phenol, or a phenol which is substituted by pyrazine methyl substituted by multi-alkyl.

A compound or the pharmaceutically acceptable salt thereof, wherein the compound is selected from:

(1) (3,5,6-trimethyl pyrazine-2-yl)methyl-4-(3,7,12-trihydroxy-10,13-dimethyl hexadecahydro-1H-cyclopenta[a]phenanthren-17-yl)pentanoate;

(2) (3,5,6-trimethyl pyrazine-2-yl)methyl-4-(3,12-dihydroxy-10,13-dimethyl hexadecahydro-1H-cyclopenta[a]phenanthren-17-yl)pentanoate;

(3) (3,5,6-trimethyl pyrazine-2-yl)methyl-10-hydroxy-2,2,6a,6b,9,9,12a-heptamethyl-1,2,3,4,4a,5,6,6a,6b,7,8,8a,9,10,11,12,12a,12b,13,14b-eicosahydropicene-4a-carboxylate, (4) (3,5,6-trimethyl pyrazine-2-yl)methyl-10-hydroxy-2,4a,6a,6b,9,9,12a-heptamethyl-13-oxo-1,2,3,4,4a,5,6,6a,6b,7,8,8a,9,10,11,12,12a,12b,13,14b-eicosahydropicene-2-carboxylate, (5) (2R)-(3,5,6-trimethyl pyrazine-2-yl)methyl-2-((14R,16R)-3-acetoxy-16-hydroxy-4,4,10,13,14-pentamethyl-2,3,4,5,6,7,10,11,12,13,14,15,16,17-tetradecahydro-1H-cyclopenta[a]phenanthren-17-yl))-6-methyl-5-methylene heptylate, (6) (3,5,6-trimethyl pyrazine-2-yl)methyl-4,5-dihydroxy-9,10-dioxo-9,10-dihydroanthracene-2-carboxylate, (7) 1,8-dihydroxy-3-methyl-6-((3,5,6-trimethyl pyrazine-2-yl)methoxy)anthracene-9,10-diketone, (8) (1E,6E)-1,7-bis(3-methoxy-4-((3,5,6-trimethyl pyrazine-2-yl)methoxy)phenyl)heptyl-1,6-diene-3,5-diketone, (9) 1-(4-methoxy-2-((3,5,6-trimethyl pyrazine-2-yl)methoxy)phenyl)methyl ketone,

(10) (3,5,6-trimethyl pyrazine-2-yl)methyl 3,4,5-trihydroxycyclohexyl-1-ene formate,

(11) 5-hydroxy-2-phenyl-6,7-bis((3,5,6-trimethyl pyrazine-2-yl)methoxy)-4H-benzopyran-4-one.

A method for synthesizing the compound of formula 1, comprising the following steps:

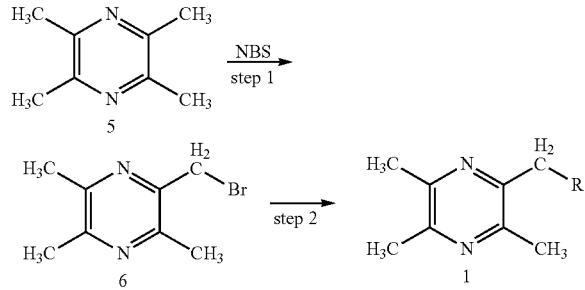

Wherein R is as defined in formula 2;

Step 1: reacting compound 5 with NBS (N-bromosuccimide) to obtain compound 6;

Step 2: reacting compound 6 with hydroxyl or carbonyl compound containing R to obtain compound 1.

Wherein the step (1) is carried out in a solvent selected from tetrachloromethane, acetonitrile and dioxane.

Wherein step (1) includes adding a radical initiator.

Wherein step (1) is carried out with the illumination of an incandescent lamp.

Wherein step (2) is carried out in a solvent selected from acetone, N,N-dimethyl formamide or tetrahydrofuran.

Wherein step (2) is carried out in the presence of a substance selected from triethylamine, kalium carbonate and piperidine.

Wherein step (2) is carried out under heating.

Specifically, the Method for Synthesizing said Compounds are as Follows:

The preparation of 2-bromomethyl-3,5,6-trimethyl pyrazine intermediate

Dehydrated tetramethylpyrazine is dissolved into an organic solvent and then NBS is added at a mole ratio of tetramethylpyrazine to NBS=1:(0.5-0.7). The reaction liquid is then refluxed to react for 10-12 h. 2-bromomethyl-3,5,6-trimethyl pyrazine is obtained as a pale-red half-oily substance after post-treatment purification.

Preferably, dehydrated tetramethylpyrazine is dissolved into $CCl_4$ and then NBS is added at a mole ratio of tetramethylpyrazine to NBS=1:0.5. Adding a small amount of benzoylperoxide as the radical initiator is preferred. The reaction liquid is then refluxed to react for 10-12 h. 2-bromomethyl-3,5,6-trimethyl pyrazine is obtained as a pale-red half-oily substance after post-treatment purification.

More preferably, dehydrated tetramethylpyrazine is dissolved into an organic solvent, preferably $CCl_4$, and then NBS is added at a mole ratio of tetramethylpyrazine to NBS=1:0.7. Then a small amount of benzoylperoxide is added as the radical initiator. The reaction is carried out under the illumination of an incandescent lamp and the reaction liquid is refluxed to react for 10-12 h. Next the reaction liquid is cooled and condensed, and the excess tetramethylpyrazine is sucked away under reduced pressure in 60-70° C. water bath. The residue is kept in a fridge for standing, and 2-bromomethyl-3,5,6-trimethyl pyrazine is obtained as a pale-red half-oily substance.

Synthesis of LQC-Y1 (Compound 1)

The prepared 2-bromomethyl-3,5,6-trimethyl pyrazine and cholic acid are added at a ratio of 1:(1-1.1) into a reaction solvent and then anhydrous kalium carbonate is added. After that the reaction liquid is agitated at 80-100° C. for 4-5 h. The reaction is carried out until the raw materials are basically disappeared. Then the reaction liquid is subjected to post-treating and separating to obtain a white powder as compound 1.

Preferably, the prepared 2-bromomethyl-3,5,6-trimethyl pyrazine and cholic acid are added at a ratio of 1:1 into DMF and then anhydrous kalium carbonate is added. After that the reaction liquid is agitated at 80° C. for 4.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 3 times. All the extract is combined and evaporated to dryness. The residue obtained is re-dissolved by a small amount of trichlormethane, and silica gel is then added into the resultant sample, and the resultant sample is evaporated to dryness at a reduced pressure and is agitated. The mixture is then eluted with benzine:ethyl acetate:methanol=15-25:3:1 as the eluent to obtain a white powder as compound 1.

More preferably, the prepared 2-bromomethyl-3,5,6-trimethyl pyrazine and cholic acid are added at a ratio of 1:1 into DMF and then anhydrous kalium carbonate is added. After that the reaction liquid is agitated at 100° C. for 4.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 3 times. All the extract is combined and evaporated to dryness. The residue obtained is re-dissolved by a small amount of trichlormethane, and silica gel is then added into the resultant sample, and the resultant sample is evaporated to dryness at a reduced pressure and is agitated. The mixture then is eluted with benzine:ethyl acetate:methanol=20:3:1 as the eluent to obtain a white powder as compound 1.

Synthesis of LQC-Y2 (Compound 2)

The prepared 2-bromomethyl-3,5,6-trimethyl pyrazine and deoxycholic acid are added at a ratio of 1:(1-1.1) into a reaction solvent and then anhydrous kalium carbonate is added. After that the reaction liquid is agitated at 80-100° C. for 4-5 h. The reaction is carried out until the raw materials are basically disappeared. Then the reaction liquid is subjected to post-treating and separating to obtain a pale yellow oily substance as the compound 2.

Preferably, the prepared 2-bromomethyl-3,5,6-trimethyl pyrazine and deoxycholic acid are added at a ratio of 1:1 into DMF and then anhydrous kalium carbonate is added. After that the reaction liquid is agitated at 80° C. for 4.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 3 times. All the extract is combined and evaporated to dryness. The residue obtained is re-dissolved by a small amount of trichlormethane, and silica gel is then added into the resultant sample, and the resultant sample is evaporated to dryness at a reduced pressure and is agitated. The mixture then is eluted with benzene:ethyl acetate=3-5:1 as the eluent to obtain a pale yellow oily substance as the compound 2.

More preferably, the prepared 2-bromomethyl-3,5,6-trimethyl pyrazine and deoxycholic acid are added at a ratio of 1:1 into DMF and then anhydrous kalium carbonate is added. After that the reaction liquid is agitated at 100° C. for 4.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 3 times. All the extract is combined and evaporated to dryness. The residue obtained is re-dissolved by a small amount of trichlormethane, and silica gel is then added into the resultant sample, and the resultant sample is evaporated to dryness at a reduced pressure and is agitated. The mixture then is eluted with benzene:ethyl acetate=4:1 as the eluent to obtain a pale yellow oily substance as the compound 2.

Synthesis of LQC-Y3 (Compound 3)

The prepared 2-bromomethyl-3,5,6-trimethyl pyrazine and oleanolic acid are added at a ratio of 1:(1-1.1) into a reaction solvent and then anhydrous kalium carbonate is added. After that the reaction liquid is agitated at 80-100° C. for 4-5 h. The reaction is carried out until the raw materials are basically disappeared. Then the reaction liquid is subjected to post-treating and separating to obtain a white powdered substance as compound 3.

Preferably, the prepared 2-bromomethyl-3,5,6-trimethyl pyrazine and oleanolic acid are added at a ratio of 1:1 into THF and then anhydrous kalium carbonate is added. After that the reaction liquid is agitated at 80° C. for 4.5 h, wherein TLC is preferably used to detect the reaction. The reaction is carried out until the raw materials are basically disappeared. Then the kalium carbonate is removed by filtration. The filtrate is condensed to contain a small amount of tetrahydrofuran, and silica gel is added into the resultant sample and the resultant sample is evaporated to dryness at a reduced pressure and is agitated. The mixture then is eluted with benzine:ethyl acetate=3-1:1 as the eluent to obtain a white powdered substance as compound 3.

More preferably, the prepared 2-bromomethyl-3,5,6-trimethyl pyrazine and oleanolic acid are added at a ratio of 1:1 into THF and then anhydrous kalium carbonate is added. After that the reaction liquid is agitated at 100° C. for 4.5 h, wherein TLC is preferably used to detect the reaction. The reaction is carried out until the raw materials are basically disappeared. The kalium carbonate is removed by filtration. The filtrate is condensed to contain a small amount of tetrahydrofuran, and silica gel is added into the resultant sample and the resultant sample is evaporated to dryness at a reduced pressure and is agitated. The mixture then is eluted with benzene:ethyl acetate=3:2 as the eluent to obtain a white powder-like substance as compound 3.

Synthesis of LQC-Y4 (Compound 4)

The prepared 2-bromomethyl-3,5,6-trimethyl pyrazine and glycyrrhetinic acid are added at a ratio of 1:(1-1.1) into a reaction solvent and then anhydrous kalium carbonate is added. After that the reaction liquid is agitated at 80-100° C. for 4-5 h. The reaction is carried out until the raw materials are basically disappeared. Then the reaction liquid is subjected to post-treating and separating to obtain a white powder as compound 4.

Preferably, the prepared 2-bromomethyl-3,5,6-trimethyl pyrazine and glycyrrhetinic acid are added at a ratio of 1:1 into DMF and then anhydrous kalium carbonate is added. After that the reaction liquid is agitated at 80° C. for 4.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 3 times. All the extract is combined and evaporated to dryness. The residue obtained is re-dissolved by a small amount of trichlormethane, and silica gel is then added into the resultant sample, and the resultant sample is evaporated to dryness at a reduced pressure and is agitated. The mixture then is eluted with benzine:acetone=10-15:1 as the eluent to obtain a white powder as compound 4.

More preferably, the prepared 2-bromomethyl-3,5,6-trimethyl pyrazine and glycyrrhetinic acid are added at a ratio of 1:1 into DMF and then anhydrous kalium carbonate is added. After that the reaction liquid is agitated at 100° C. for 4.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 3 times. All the extract is combined and evaporated to dryness. The residue obtained is re-dissolved by a small amount of trichlormethane, and silica gel is then added into the resultant sample, and the resultant sample is evaporated to dryness at a reduced pressure and is agitated. The mixture then is eluted with benzene:acetone=10:1 as the eluent to obtain a white powder as compound 4.

Synthesis of LQC-Y5 (Compound 5)

The prepared 2-bromomethyl-3,5,6-trimethyl pyrazine and pachymic acid are added at a ratio of 1:(1-1.1) into a reaction solvent and then anhydrous kalium carbonate is added. After that the reaction liquid is agitated at 80-100° C. for 3-5 h. The reaction is carried out until the raw materials are basically disappeared. Then the reaction liquid is subjected to post-treating and separating to obtain compound 5.

Preferably, the prepared 2-bromomethyl-3,5,6-trimethyl pyrazine and pachymic acid are added at a ratio of 1:1 into DMF and then anhydrous kalium carbonate is added. After that the reaction liquid is agitated at 80° C. for 4.5 h, wherein TLC is preferably used to detect the reaction. The reaction is carried out until the raw materials are basically disappeared. Saturated sodium bicarbonate solution is added into the reaction liquid and then the resultant reaction liquid is extracted by ethyl acetate for 4 times. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzine:acetone=15-25:1 as the eluent to obtain a pale yellow oily substance as compound 5.

More preferably, the prepared 2-bromomethyl-3,5,6-trimethyl pyrazine and pachymic acid are added at a ratio of 1:1 into DMF and then anhydrous kalium carbonate is added. After that the reaction liquid is agitated at 100° C. for 4.5 h, wherein TLC is preferably used to detect the reaction. The reaction is carried out until the raw materials are basically disappeared. Saturated sodium bicarbonate solution is added into the reaction liquid and then the resultant reaction liquid is extracted by ethyl acetate for 3 times. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzene:acetone=20:1 as the eluent to obtain a pale yellow oily substance as compound 5.

Synthesis of LQC-Y6 (Compound 6)

The prepared 2-bromomethyl-3,5,6-trimethyl pyrazine and emodic acid are added at a ratio of 1: (1-1.1) into a reaction solvent and then anhydrous kalium carbonate is added. After that the reaction liquid is agitated at 80-100° C. for 4-6 h. The reaction is carried out until the raw materials are basically disappeared. Then the reaction liquid is subjected to post-treating and separating to obtain compound 6.

Preferably, the prepared 2-bromomethyl-3,5,6-trimethyl pyrazine and emodic acid are added at a ratio of 1:1 into DMF and then anhydrous kalium carbonate is added. After that the reaction liquid is agitated under reflux for 5.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 4 times. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzene:ethyl acetate=10:1-2 as the eluent to obtain a yellow powder as compound 6.

More preferably, the prepared 2-bromomethyl-3,5,6-trimethyl pyrazine and emodic acid are added at a ratio of 1:1 into DMF and then anhydrous kalium carbonate is added. After that the reaction liquid is agitated under reflux for 4.5 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzene:ethyl acetate=10:1 as the eluent to obtain a yellow powder as compound 6.

Synthesis of LQC-Y 7 (Compound 7)

The prepared 2-bromomethyl-3,5,6-trimethyl pyrazine and emodin are added at a ratio of 1: (1-1-1.1) into a reaction solvent and then anhydrous kalium carbonate is added. After that the reaction liquid is agitated at 70-90° C. for 2-4 h. The reaction is carried out until the raw materials are basically disappeared. Then the reaction liquid is subjected to post-treating and separating to obtain compound 7.

Preferably, the prepared 2-bromomethyl-3,5,6-trimethyl pyrazine and emodin are added at a ratio of 1:1.05 into DMF and then anhydrous kalium carbonate is added. After that the reaction liquid is agitated at 70° C. for 2 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate for 4 times. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzene:ethyl acetate=10-15:1 as the eluent to obtain a yellow powder as compound 7.

More preferably, the prepared 2-bromomethyl-3,5,6-trimethyl pyrazine and emodin are added at a ratio of 1:1 into DMF and then anhydrous kalium carbonate is added. After that the reaction liquid is agitated at 80° C. for 3 h, wherein TLC is preferably used to detect the reaction. The reaction is carried out until the raw materials are basically disappeared. Saturated sodium chloride solution is added into the reaction liquid and then the resultant reaction liquid is extracted by ethyl acetate. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzene:ethyl acetate=10:1 as the eluent to obtain a yellow powder as compound 7.

Synthesis of LQC-Y8 (Compound 8)

The prepared 2-bromomethyl-3,5,6-trimethyl pyrazine and curcumin are added at a ratio of 2: (1-1.1) into a reaction solvent and then anhydrous kalium carbonate is added. After that the reaction liquid is agitated at 50-70° C. for 2-4 h. The reaction is carried out until the raw materials are basically disappeared. Then the reaction liquid is subjected to post-treating and separating to obtain compound 8.

Preferably, the prepared 2-bromomethyl-3,5,6-trimethyl pyrazine and curcumin are added at a ratio of 2:1.05 into acetone and then anhydrous kalium carbonate is added. After that the reaction liquid is agitated at 70° C. for 2 h, wherein TLC is preferably used to detect the reaction. The reaction is carried out until the raw materials are basically disappeared. The reaction liquid is evaporated to dryness, and silica gel is then added into the resultant sample, the resultant sample is evaporated to dryness at a reduced pressure and is agitated. The mixture then is eluted with benzine: acetone=2-6:1 as the eluent to obtain a yellow powder as compound 8.

More preferably, the prepared 2-bromomethyl-3,5,6-trimethyl pyrazine and curcumin are added at a ratio of 2:1 into acetone and then anhydrous kalium carbonate is added. After that the reaction liquid is agitated at 65° C. for 3 h, wherein TLC is preferably used to detect the reaction. The reaction is carried out until the raw materials are basically disappeared. The reaction liquid is evaporated to dryness, and silica gel is then added into the resultant sample, the resultant sample is evaporated to dryness at a reduced pressure and is agitated. The mixture then is eluted with benzene:acetone=4:1 as the eluent to obtain a yellow powder as compound 8.

Synthesis of LQC-Y9 (Compound 9)

The prepared 2-bromomethyl-3,5,6-trimethyl pyrazine and paeonol are added at a ratio of 1:(1-1.1) into a reaction solvent and then anhydrous kalium carbonate is added. After that the reaction liquid is agitated at 70-95° C. for 2-4 h. The reaction is carried out until the raw materials are basically disappeared. Then the reaction liquid is subjected to post-treating and separating to obtain a white prismatioc crystal as compound 9.

Preferably, the prepared 2-bromomethyl-3,5,6-trimethyl pyrazine and paeonol are added at a ratio of 1:1.05 into DMF and then anhydrous kalium carbonate is added. After that the reaction liquid is agitated at 70° C. for 2 h, wherein TLC is preferably used to detect the reaction. The reaction is carried out until the raw materials are basically disappeared. Saturated sodium bicarbonate aqueous solution is added into the reaction liquid to dilute and then the resultant reaction liquid is extracted by ethyl acetate. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzine:ethyl acetate=6-10:1 as the eluent and the raw product obtained is crystallized using acetone-cyclohexane to obtain a white prismatioc crystal as compound 9.

More preferably, the prepared 2-bromomethyl-3,5,6-trimethyl pyrazine and paeonol are added at a ratio of 1:1 into DMF and then anhydrous kalium carbonate is added. After that the reaction liquid is agitated at 85° C. for 3 h, wherein TLC is preferably used to detect the reaction. The reaction is carried out until the raw materials are basically disappeared. Saturated sodium bicarbonate aqueous solution is added into the reaction liquid to dilute and then the resultant reaction liquid is extracted by ethyl acetate. All the extract is combined and evaporated to dryness. The residue obtained is re-dissolved by a small amount of acetone, and silica gel is then added into the resultant sample, and the resultant sample is evaporated to dryness at a reduced pressure and is agitated. The mixture then is eluted with benzene:ethyl acetate=7:1 as the eluent and the raw product obtained is crystallized using acetone-cyclohexane to obtain a white prismatioc crystal as compound 8.

Synthesis of LQC-Y10 (Compound 10)

The prepared 2-bromomethyl-3,5,6-trimethyl pyrazine and shikimic acid are added at a ratio of 1:(1-1.1) into a reaction solvent and then triethyl amine is added. After that the reaction liquid is agitated under reflux for 2-4 h. The reaction is carried out until the raw materials are basically disappeared. Then the reaction liquid is subjected to post-treating and separating to obtain compound 10.

Preferably, the prepared 2-bromomethyl-3,5,6-trimethyl pyrazine and shikimic acid are added at a ratio of 1:1.05 into DMF and then triethyl amine is added. After that the reaction liquid is agitated under reflux for 2 h, wherein TLC is preferably used to detect the reaction. The reaction is carried out until the raw materials are basically disappeared. Then ethyl acetate is added into the reaction liquid. The resultant reaction liquid is condensed and the obtained residue is dissolved by a solvent. And silica gel is then added into the resultant sample, and the resultant sample is agitated. The mixture then is eluted with benzene:acetone=5:1-4 as the eluent to obtain a white powder as compound 10.

More preferably, the prepared 2-bromomethyl-3,5,6-trimethyl pyrazine and shikimic acid are added at a ratio of 1:1.1 into DMF and then triethyl amine is added. After that the reaction liquid is agitated under reflux for 3 h, wherein TLC is preferably used to detect the reaction. The reaction is carried out until the raw materials are basically disappeared. Then ethyl acetate is added into the reaction liquid. The resultant reaction liquid is condensed at a reduced pressure and the obtained residue is dissolved by methanol. And silica gel is then added into the resultant sample, and the resultant sample is evaporated to dryness at a reduced pressure and is agitated. The mixture then is eluted with benzene:acetone=5:3 as the eluent to obtain a white powder as compound 10.

Synthesis of LQC-Y11 (Compound 11)

The prepared 2-bromomethyl-3,5,6-trimethyl pyrazine and baicalin are added at a ratio of 2:(0.9-1.1) into a reaction solvent and then kalium carbonate is added. After that the reaction liquid is agitated at 90-100° C. for 5-7 h. The reaction is carried out until the raw materials are basically disappeared. Then the reaction liquid is subjected to post-treating and separating to obtain compound 11.

Preferably, the prepared 2-bromomethyl-3,5,6-trimethyl pyrazine and baicalin are added at a ratio of 2:0.95 into DMF and acetone and then anhydrous kalium carbonate is added. After that the reaction liquid is agitated at 90° C. for 7 h, wherein TLC is preferably used to detect the reaction. The reaction is carried out until the raw materials are basically disappeared. Unsaturated sodium bicarbonate aqueous solution is added into the reaction liquid to dilute and then the resultant reaction liquid is extracted by ethyl acetate. All the extract is combined and evaporated to dryness. The residue obtained is re-dissolved by a small amount of solvent, and silica gel is then added into the resultant sample, and the resultant sample is evaporated to dryness at a reduced pressure and is agitated. The mixture then is eluted with benzene:acetone=6-8:1 as the eluent to obtain a pale yellow powder as compound 11.

More preferably, the prepared 2-bromomethyl-3,5,6-trimethyl pyrazine and baicalin are added at a ratio of 2:1 into DMF and acetone and then anhydrous kalium carbonate is added. After that the reaction liquid is agitated at 95° C. for 6 h under $N_2$ protection, wherein TLC is preferably used to detect the reaction. The reaction is carried out until the raw materials are basically disappeared. 5% sodium bicarbonate aqueous solution is added into the reaction liquid and then the resultant reaction liquid is extracted by ethyl acetate. All the extract is combined and evaporated to dryness. The residue obtained is re-dissolved by a small amount of trichlormethane and silica gel is then added into the resultant sample, and the resultant sample is evaporated to dryness at a reduced pressure and is agitated. The mixture then is eluted with benzene:acetone=7:1 as the eluent to obtain a pale yellow powder as compound 11.

DETAILED DESCRIPTION OF THE PREFERRED EMBODIMENT

The examples of the compounds of the present invention are provided as below; however, these examples can not be comprehended as limitations to the present invention.

Preparation Example 1

The preparation of 2-bromomethyl-3,5,6-trimethyl pyrazine intermediate

Dehydrated tetramethylpyrazine 10 g was dissolved into $CCl_4$ 60 ml and then NBS 9.17 g was added at a mole ratio of tetramethylpyrazine to NBS=1:0.7 (a minute amount of benzoylperoxide can be added as radical initiator). Reaction was carried out under reflux under the illumination of an incandescent lamp for 10-12 h. The reaction sample was cooled and condensed, and the excess tetramethylpyrazine was sucked away at a reduced pressure in 60-70° C. water bath. The residue was kept in a fridge for standing and a pale red half-oily substance 7.75 g was obtained with a yield of 70%.

Preparation Example 2

Synthesis of LQC-Y1 (Compound 1)

2-bromomethyl-3,5,6-trimethyl pyrazine 1.63 mmol prepared in example 1 and cholic acid 1.63 mmol were put into a 100 ml three-necked flask and then DMF 40 ml was added. Anhydrous kalium carbonate 9 mmol was added after the mixture was dissolved. The reaction liquid was agitated at 90° C. for 4.5 h. The reaction was stopped when the raw materials were basically disappeared by the detection of TLC. Next, saturated sodium chloride solution 250 ml was added into the reaction liquid and then the resultant reaction liquid was extracted by ethyl acetate for 3 times. All the extract was combined and evaporated to dryness. The residue was re-dissolved by a small amount of trichlormethane, silica gel 3 g was added thereinto, and the resultant sample was evaporated to dryness at a reduced pressure and was agitated. The obtained mixture was eluted with benzene:ethyl acetate:methanol=20:3:1 as the eluent to obtain a white powder 0.44 g. The yield was 50%, FAB-MS m/z 543 [M+H]$^+$ and the melting point was 67.9-68.8° C.; the hydrogen spectrum and carbon spectrum NMR data of compound 1 were as follows:

$^1$HNMR (500 MHZ, CDCl$_3$): 0.670 (s, 3H, 18'-CH$_3$), 0.893 (s, 3H, 19'-CH$_3$), 0.980 (d, 3H, 21'-CH$_3$), 3.453 (m, 1H, 3β'-CH), 3.852 (m, 1H, 7β-CH), 3.965 (m, 1H, 12β-CH), 5.205 (s, 2H, O—CH$_2$), 2.557 (s, 3H, 6-CH$_3$), 2.540 (s, 3H, 5-CH$_3$), 2.526 (s, 3H, 3-CH$_3$), 1.000~2.500 (24H, the hydrogen signal of methylene and methenyl in steroid parent nucleus structure);

$^{13}$CNMR (125 MHZ, CDCl$_3$): 35.3 (C-1), 30.5 (C-2), 71.9 (C-3), 39.6 (C-4), 41.5 (C-5), 34.8 (C-6), 68.5 (C-7), 39.5 (C-8), 26.4 (C-9), 34.7 (C-10), 28.2 (C-11), 73.0 (C-12), 46.5 (C-13), 41.8 (C-14), 23.3 (C-15), 27.5 (C-16), 47.0 (C-17), 12.5 (C-18), 22.5 (C-19), 35.3 (C-20), 17.3 (C-21), 30.9 (C-22), 31.1 (C-23), 174.0 (24-COOH), 64.9 (O—CH$_2$—); δC of pyrazine ring: 151.1 (C-2), 145.1 (C-3), 148.9 (C-5), 149.2 (C-6), 21.6 (6-CH$_3$), 21.5 (5-CH$_3$), 20.4 (3-CH$_3$).

Preparation Example 3

Synthesis of LQC-Y2 (Compound 2)

2-bromomethyl-3,5,6-trimethyl pyrazine 3.26 mmol prepared in example 1 and deoxycholic acid 3.26 mmol were put into a 100 ml three-necked flask and then DMF 40 ml was added. Anhydrous kalium carbonate 9 mmol was added after the mixture was dissolved. The reaction liquid was agitated at 85° C. for 4 h. The reaction was stopped when the raw materials were basically disappeared by the detection of TLC. Next, saturated sodium chloride solution 250 ml was added into the reaction liquid and then the resultant reaction liquid was extracted by ethyl acetate for 3 times. All the extract was combined and evaporated to dryness. The residue was re-dissolved by a small amount of trichlormethane, silica gel 3 g was added thereinto, and the resultant sample was evaporated to dryness at a reduced pressure and was agitated. The obtained mixture was eluted with benzine:ethyl acetate=10:2.5 as the eluent to obtain a pale yellow oily substance 1.0 g. The yield was 58.4%, FAB-MS m/z 527 [M+H]$^+$; the hydrogen spectrum and carbon spectrum NMR data of compound 2 were as follows:

$^1$HNMR (500 MHZ, CDCl$_3$): 0.652 (s, 3H, 18, —CH$_3$), 0.901 (s, 3H, 19, —CH$_3$), 0.954 (d, 3H, 21, —CH$_3$), 3.605 (m, 1H, 3, β-CH), 3.958 (m, 1H, 12, β-CH), 5.187 (s, 2H$_2$O—CH$_2$), 2.532 (s, 3H, 6-CH$_3$), 2.516 (s, 3H, 5-CH$_3$), 2.503 (s, 3H, 3-CH$_3$), 1.000~2.500 (26H, the hydrogen signal of methylene and methenyl in steroid parent nucleus structure);

$^{13}$CNMR (125 MHZ, CDCl$_3$): 35.1 (C-1), 30.5 (C-2), 71.8 (C-3), 36.4 (C-4), 42.1 (C-5), 27.1 (C-6), 26.1 (C-7), 36.0 (C-8), 33.7 (C-9), 34.1 (C-10), 28.7 (C-11), 73.1 (C-12), 46.5 (C-13), 48.3 (C-14), 23.6 (C-15), 27.4 (C-16), 47.3 (C-17), 12.7 (C-18), 23.1 (C-19), 35.2 (C-20), 17.3 (C-21), 31.1 (C-22), 30.9 (C-23), 165.9 (24-COOH), 64.5 (O—CH$_2$—); δC of pyrazine ring: 151.1 (C-2), 145.0 (C-3), 148.8 (C-5), 149.1 (C-6), 21.5 (6-CH$_3$), 21.4 (5-CH$_3$), 20.4 (3-CH$_3$).

Preparation Example 4

Synthesis of LQC-Y3 (Compound 3)

2-bromomethyl-3,5,6-trimethyl pyrazine 3.26 mmol prepared in example 1 and oleanolic acid 3.26 mmol were put into a 150 ml three-necked flask and then tetrahydrofuran solvent 80 ml was added. Then kalium carbonate 9 mmol was added. The reaction liquid was heated and refluxed for 2.5 h. The reaction was stopped when the raw materials were basically disappeared by the detection of TLC. Next, the kalium carbonate was removed by filtration. The filtrate was condensed to contain a small amount of tetrahydrofuran, silica gel 4 g was added thereinto, and the resultant sample was evaporated to dryness at a reduced pressure and was agitated. The obtained mixture was eluted with benzene:ethyl acetate=3:2 as the eluent to obtain a white powder 1.26 g. The yield was 65.6%, FAB-MS m/z 591 [M+H]$^+$; and the melting point was 133.8-134.4° C.; the hydrogen spectrum and carbon spectrum NMR data of compound 3 were as follows:

$^1$HNMR (500 MHZ, CDCl$_3$): 0.552, 0.799, 0.895, 0.907, 0.927, 1.002, 1.127 (s, 21H, 7×CH$_3$), 3.225 (m, 1H, 3, β-CH), 5.257 (brs, 1H, 12-CH), 5.257 (q, 2H$_2$O—CH$_2$), 2.575 (s, 3H, 6-CH$_3$), 2.536 (s, 3H, 5-CH$_3$), 2.516 (s, 3H, 3-CH$_3$), 1.000~2.500 (23H, the hydrogen signal of methylene and methenyl in triterpene parent nucleus structure);

$^{13}$CNMR (125 MHZ, CDCl$_3$): 38.4 (C-1), 27.2 (C-2), 79.0 (C-3), 38.8 (C-4), 55.2 (C-5), 18.3 (C-6), 33.1 (C-7), 39.2 (C-8), 47.6 (C-9), 37.0 (C-10), 23.7 (C-11), 122.5 (C-12), 143.6 (C-13), 41.7 (C-14), 27.6 (C-15), 23.1 (C-16), 46.9 (C-17), 41.3 (C-18), 45.9 (C-19), 30.7 (C-20), 33.9 (C-21), 32.7 (C-22), 28.1 (C-23), 15.6 (C-24), 15.3 (C-25), 16.8 (C-26), 25.9 (C-27), 177.2 (C-28), 32.4 (C-29), 23.4 (C-30), 64.9 (O—CH$_2$—); δC of pyrazine ring: 150.9 (C-2), 145.5 (C-3), 148.9 (C-5), 149.1 (C-6), 21.6 (6-CH$_3$), 21.4 (5-CH$_3$), 20.5 (3-CH$_3$).

Preparation Example 5

Synthesis of LQC-Y4 (Compound 4)

2-bromomethyl-3,5,6-trimethyl pyrazine 1.09 mmol prepared in example 1 and glycyrrhetinic acid 1.09 mmol were put into a 25 ml three-necked flask and then DMF 15 ml was added. Kalium carbonate 3 mmol was added after the mixture was dissolved. The reaction liquid was heated and refluxed for 5.5 h. The reaction balance was monitored by the detection of TLC. Next, after the reaction was finished, the kalium carbonate was removed by filtration. Saturated sodium chloride solution 100 ml was added into the reaction liquid and then the resultant reaction liquid was extracted by ethyl acetate for 3 times. All the extract was combined and evaporated to dryness. The residue obtained was re-dissolved by a small amount of trichlormethane, silica gel 2 g was added thereinto, and the resultant sample was evaporated to dryness at a reduced pressure and was agitated. The obtained mixture was eluted with benzene:acetone=12:1 as the eluent to obtain a white powder 0.33 g. The yield was 50.1%, FAB-MS m/z 605 [M+H]$^+$; and the melting point was 91.7-92.9° C.; the hydrogen spectrum and carbon spectrum NMR data of compound 4 were as follows:

$^1$HNMR (500 MHZ, CDCl$_3$): 0.809, 0.815, 1.011, 1.126, 1.141, 1.204, 1.368 (s, 21H, 7×CH$_3$), 3.233 (dd, 1H, 3-CH), 5.552 (s, 1H, 12-CH), 5.229 (q, 2H₂O—CH₂), 2.558 (s, 3H, 6-CH₃), 2.545 (s, 3H, 5-CH₃), 2.527 (s, 3H,3-CH₃), 1.000-3.000 (21H, the hydrogen signal of methylene and methenyl in triterpene parent nucleus structure);

$^{13}$CNMR (125 MHZ, CDCl₃): 39.1 (C-1), 27.3 (C-2), 78.8 (C-3), 41.1 (C-4), 54.9 (C-5), 17.5 (C-6), 31.2 (C-7), 43.2 (C-8), 61.8 (C-9), 32.7 (C-10), 200.1 (C-11), 128.5 (C-12), 169.0 (C-13), 45.4 (C-14), 26.5 (C-15), 30.99 (C-16), 31.9 (C-17), 48.0 (C-18), 37.7 (C-19), 44.2 (C-20), 28.5 (C-21), 37.1 (C-22), 28.1 (C-23), 15.6 (C-24), 18.7 (C-25), 16.4 (C-26), 26.4 (C-27), 23.4 (C-28), 28.5 (C-29), 176.1 (C-30), 64.9 (O—CH₂—); δC of pyrazine ring: 151.0 (C-2), 145.2 (C-3), 148.3 (C-5), 149.4 (C-6), 21.6 (6-CH₃), 21.5 (5-CH₃), 20.4 (3-CH₃).

Preparation Example 6

Synthesis of LQC-Y5 (Compound 5)

2-bromomethyl-3,5,6-trimethyl pyrazine 0.3 mmol prepared in example 1 and pachymic acid 0.3 mmol were put into a 25 ml three-necked flask and then DMF 14 ml was added. Kalium carbonate 5 mmol was added after the mixture was dissolved. The reaction liquid was heated at 85° C. for 3 h. The reaction was stopped when the raw materials were basically disappeared by the detection of TLC. Next, the kalium carbonate was removed by filtration. Saturated sodium bicarbonate aqueous solution was added into the reaction liquid and then the resultant reaction liquid was extracted by ethyl acetate for 4 times. All the extract was combined and evaporated to dryness. The residue obtained was re-dissolved by a small amount of acetone, silica gel 1.5 g was added thereinto, and the resultant sample was evaporated to dryness at a reduced pressure and was agitated. The obtained mixture was eluted with benzene:acetone=20:1 as the eluent to obtain a pale yellow substance 0.05 g. The yield was 25.2%, FAB-MS m/z 663 [M+H]⁺; the hydrogen spectrum and carbon spectrum NMR data of compound 5 were as follows:

$^1$HNMR (500 MHZ, CDCl₃): 0.892 (3H, s, H-28); 0.955 (3H, s, H-29); 0.968 (3H, s, H-19); 0.979 (3H, s, H-26); 0.984 (3H, s, H-27); 0.992 (3H, s, H-18); 1.102 (3H, s, H-30); 2.068 (s, 3H, acetyloxy); 4.119 (m, 1H, H-16); 4.505 (dd, 1H, H-3); 4.67 (s, 1H, H-31); 4.74 (s, 1H, H-31); 5.226 (dd, 2H, J=5.05 Hz, O—CH₂); 2.590 (s, 3H, 6-CH₃); 2.522 (brs, 6H, 3,5-CH₃); 1.000-2.500 (22H, the hydrogen signal of methylene and methenyl in triterpene parent nucleus structure).

$^{13}$CNMR (125 MHZ, CDCl₃): 35.3 (C-1), 24.1 (C-2), 80.8 (C-3), 37.8 (C-4), 50.4 (C-5), 18.0 (C-6), 26.4 (C-7), 134.3 (C-8), 134.2 (C-9), 36.9 (C-10), 20.6 (C-11), 29.7 (C-12), 46.7 (C-13), 49.2 (C-14), 42.7 (C-15), 76.8 (C-16), 56.9 (C-17), 17.5 (C-18), 19.2 (C-19), 48.1 (C-20), 175.5 (COOH-21), 32.2 (C-22), 33.7 (C-23), 155.0 (24-C), 35.2 (25-C), 21.8 (26-C), 21.7 (27-C), 28.0 (28-C), 16.9 (29-C), 25.2 (30-C), 106.9 (31-C), 21.3 (CH₃CO), 171.0 (CH₃CO), 64.6 (O—CH₂—); δC of pyrazine ring: 151.3 (C-2), 144.9 (C-3), 149.0 (C-5), 149.1 (C-6), 21.4 (6-CH₃), 21.3 (5-CH₃), 20.5 (3-CH₃).

Preparation Example 7

Synthesis of LQC-Y6 (Compound 6)

2-bromomethyl-3,5,6-trimethyl pyrazine 2.16 mmol prepared in example 1 and emodic acid 2.16 mmol were put into a 50 ml round bottom flask and then DMF 25 ml was added. Triethyl amine 3 mmol was added after the mixture was dissolved. The reaction liquid was heated and refluxed for 5.5 h. The reaction was stopped when the raw materials were basically disappeared by the detection of TLC. Next, Saturated sodium chloride solution 150 ml was added into the reaction liquid and then the precipitation was filtrated. The residue is dissolved by trichlormethane 4.5 ml, silica gel 3.3 g was added thereinto, and the resultant sample was evaporated to dryness at a reduced pressure and was agitated. The obtained mixture was eluted with benzine:ethyl acetate=10:1.7 as the eluent to obtain a yellow powder 0.42 g. The yield was 46.5%, FAB-MS m/z 419 [M+H]⁺; and the melting point was 220.7-221.6° C.; the hydrogen spectrum and carbon spectrum NMR data of compound 6 were as follows:

$^1$HNMR (500 MHZ, CDCl₃): 12.042 (s, 1H, 8-OH), 11.975 (s, 1H, 1-OH), 8.434 (d, 1H, 4-H), 7.964 (d, 1H, 2-H), 7.878 (d,1H, 5-H), 7.352 (d,1H, 7-H), 7.746 (t, 1H, 6-H), 5.521 (s, 2H₂O—CH₂), pyrazine ring; 2.642 (s, 3H, 6-CH₃), 2.588 (s, 3H, 5-CH₃), 2.557 (s, 3H, 3-CH₃);

$^{13}$CNMR (125 MHZ, CDCl₃): anthraquinone parent nucleus 92.8 (C-9), 180.9 (C-10), 162.4 (C-1), 162.91 (C-8), 164.1 (—COOH), 137.8 (C-3), 137.5 (C-6), 134.0 (C-11), 133.5 (C-14), 125.5 (C-7), 124.9 (C-4), 120.44 (C-5), 120.39 (C-2), 118.4 (C-13), 115.8 (C-12), 66.5 (CH₂—O—) δC of pyrazine ring: 151.7 (C-2), 144.3 (C-3), 149.0 (C-5), 149.5 (C-6), 21.6 (6-CH₃), 21.5 (5-CH₃), 20.5 (3-CH₃).

Preparation Example 8

Synthesis of LQC-Y7 (Compound 7)

2-bromomethyl-3,5,6-trimethyl pyrazine 1.11 mmol prepared in example 1 and emodin 1.11 mmol were put into a 20 ml three-necked flask and then DMF 13 ml was added. Anhydrous kalium carbonate 0.7 g was added after the mixture was dissolved. The reaction liquid was agitated at 80° C. for 3 h. The reaction was stopped when the raw materials were basically disappeared by the detection of TLC. Next, water 60 ml was added into the reaction liquid and then the resultant reaction liquid was extracted by ethyl acetate for 3 times. All the extract was combined and evaporated to dryness. The residue was re-dissolved by a small amount of trichlormethane, silica gel 4.0 g was added thereinto, and the resultant sample was evaporated to dryness at a reduced pressure and was agitated. The obtained mixture was eluted with benzene:ethyl acetate=12:1 as the eluent to obtain a yellow powder 0.21 g. The yield was 46.9%, FAB-MS m/z 405 [M+H]⁺; the melting point was 211.7~212.8° C.; the hydrogen spectrum and carbon spectrum NMR data of compound 7 were as follows:

$^1$HNMR (500 MHZ, CDCl₃): 12.321 (s, 1H, 1-OH), 12.115 (s, 1H, 8-OH), 7.638 (s, 1H, 5-H), 7.482 (d, 1H, 4-H), 7.097 (s, 1H, 7-H), 6.853 (d,1H, 2-H), 2.198 (s, 3H, Ar—CH₃) 5.298 (s, 2H₂O—CH₂); pyrazine ring 2.616 (s, 3H, 6-CH₃), 2.562 (s, 6H, 3,5-CH₃);

$^{13}$CNMR (125 MHZ, CDCl₃): anthraquinone parent nucleus 190.8 (C-9), 181.9 (C-10), 165.4 (C-3), 165.1 (C-8), 162.5 (C-3), 148.5 (C-6), 135.3 (C-11), 133.2 (C-14), 127.5 (C-7), 121.3 (C-5), 113.7 (C-12), 110.6 (C-13), 108.8 (C-4), 107.8 (C-2), 21.4 (—CH₃), 70.5 (CH₂—O—); δC of pyrazine ring: 152.0 (C-2), 144.2 (C-3), 149.0 (C-5), 150.0 (C-6), 22.2 (6-CH₃), 21.8 (5-CH₃), 20.6 (3-CH₃).

Preparation Example 9

Synthesis of LQC-Y8 (Compound 8)

2-bromomethyl-3,5,6-trimethyl pyrazine 3.07 mmol prepared in example 1 and curcumin 1.535 mmol were put into a 20 ml three-necked flask and then acetone 13 ml was added. Anhydrous kalium carbonate 0.7 g was added after the mixture was dissolved. The reaction liquid was agitated and refluxed at 65° C. for 3 h. The reaction was stopped when the raw materials were basically disappeared by the detection of TLC. Next, the reaction liquid was evaporated to dryness, silica gel 4.0 g was added thereinto, and the resultant sample was evaporated to dryness at a reduced pressure and was agitated. The obtained mixture was eluted with benzene:acetone=4:1 as the eluent to obtain a yellow powder A: 0.44 g. The yield was 43.4%, FAB-MS m/z 637 [M+H]$^+$; the melting point was 102.7~103.8° C.; the hydrogen spectrum and carbon spectrum NMR data of compound 8 were as follows:

$^1$HNMR (500 MHZ, CDCl$_3$): 3.917 (s, 6H, OCH$_3$), 5.833 (s, 2H, 10-H), 6.516 (d,2H, J=15.5 Hz, 8,8'-H), 7.615 (d,2H, J=15.5 Hz, 7,7'-H), 7.703~7.141 (m, 6H, Ar—H) 5.269 (s, 4H, O—CH$_2$); pyrazine ring 2.641 (s, 6H, 6-CH$_3$), 2.630 (s, 12H, 3,5-CH$_3$);

$^{13}$CNMR (125 MHZ, CDCl$_3$): curcumin parent nucleus 122.3 (C-1,1'), 113.8 (C-2,2'), 150.2 (C-3,3'), 148.6 (C-4,4'), 110.4 (C-5,5'), 130.4 (C-6,6'), 140.3 (C-7,7'), 128.7 (C-8,8'), 183.2 (C-9,9'), 101.4 (C-10,10'), 56.0 (C-11,11'), 70.9 (two CH$_2$—O—); δC of two symmetric pyrazine rings: 151.4 (C-2), 145.3 (C-3), 149.9 (C-5), 150.0 (C-6), 21.7 (6-CH$_3$), 21.4 (5-CH$_3$), 20.7 (3-CH$_3$).

Preparation Example 10

Synthesis of LQC-Y9 (Compound 9)

2-bromomethyl-3,5,6-trimethyl pyrazine 30.17 mmol prepared in example 1 and paeonol 30.17 mmol were put into a 50 ml three-necked flask and then DMF 30 ml was added. Anhydrous kalium carbonate 4.5 g was added after the mixture was dissolved. The reaction liquid was agitated under reflux at 90° C. for 2.5 h. The reaction was stopped when the raw materials were basically disappeared by the detection of TLC. Next, saturated sodium bicarbonate aqueous solution was added into the reaction liquid to dilute and then the resultant reaction liquid is extracted by ethyl acetate for 2 times. All the extract is combined and evaporated to dryness. The residue was re-dissolved by a small amount of acetone, silica gel 4.0 g was added thereinto, and the resultant sample was evaporated to dryness at a reduced pressure and was agitated. The obtained mixture was eluted with benzine:ethyl acetate=7:1 as the eluent and then the obtained raw product was crystallized using acetone-cyclohexane to obtain a white prismatic crystal 4.74 g. The yield was 52.6%, FAB-MS m/z 301 [M+H]$^+$ and the melting point was 126-126.5° C.; the hydrogen spectrum and carbon spectrum NMR data of compound 9 were as follows:

$^1$HNMR (500 MHZ, CDCl$_3$): 3.875 (s, 3H$_2$OCH$_3$), 2.508 (s, 3H, OC—CH$_3$), 5.262 (s, 2H$_2$O—CH$_2$), 7.845 (d, 1H, J=8.5 Hz, Ar-3), 6.746 (d,1H, J=2 Hz, Ar-6), 6.556 (dd, 1H, J=8.5 Hz, J=2 Hz, Ar-4); pyrazine ring 2.625 (s, 3H, 6-CH$_3$), 2.599 (s, 3H, 5-CH$_3$), 2.545 (s, 3H, 3-CH$_3$);

$^{13}$CNMR (125 MHZ, CDCl$_3$): 197.5 (—C=O), 160.0 (Ar—C-1), 121.2 (Ar—C-2), 132.7 (Ar—C-3), 106.1 (Ar—C-4), 164.4 (Ar—C-5), 99.3 (Ar—C-6), 70.3 (—CH$_2$—O), 55.6 (O—CH$_3$), 32.0 (—CH$_3$), δC of pyrazine ring: 151.7 (C-2), 144.9 (C-3), 148.9 (C-5), 149.8 (C-6), 21.8 (6-CH$_3$), 21.5 (5-CH$_3$), 20.6 (3-CH$_3$).

Preparation Example 11

Synthesis of LQC-Y10 (Compound 10)

2-bromomethyl-3,5,6-trimethyl pyrazine 3.26 mmol prepared in example 1 and shikimic acid 3.4 mmol were put into a 50 ml round bottom flask and then DMF 30 ml was added. Triethyl amine 3 mmol was added after the mixture was dissolved. The reaction liquid was heated and refluxed for 3.5 h. The reaction was stopped when the raw materials were basically disappeared by the detection of TLC. Next, ethyl acetate 30 ml was added into the reaction liquid. Then the resultant reaction liquid was condensed at a reduced pressure and the residue was dissolved by methanol 4 ml. Silica gel 2.8 g was added thereinto, and the resultant sample was evaporated to dryness at a reduced pressure and was agitated. The obtained mixture was eluted with benzene:acetone=5:3 as the eluent to obtain a white powder 0.46 g. The yield was 43.8%, and the melting point was 184.3-185.4° C.; the hydrogen spectrum and carbon spectrum NMR data of compound 10 were as follows:

$^1$HNMR (500 MHZ, DMSO-d$^6$): 6.601 (d, 1H, 2-H), 5.196 (s, 2H$_2$O—CH$_2$), 4.618 (brs, 1H, 3-H), 4.199 (brs, 1H, 4-H), 3.835 (brs, 1H, 5-H), 3.559 (brs, 1H, 6e-H), 2.042 (dd, 1H, 6a-H); pyrazine ring 2.450 (s, 3H, 6-CH$_3$), 2.422 (s, 3H, 5-CH$_3$), 2.407 (s, 3H, 3-CH$_3$);

$^{13}$CNMR (125 MHZ, DMSO-d6): 166.3 (—COOH), 140.8 (C-1), 127.6 (C-2), 70.4 (C-3), 67.3 (C-4), 65.9 (C-5), 30.0 (C-6), 65.2 (—CH$_2$—O), δC of pyrazine ring: 151.4 (C-2), 145.2 (C-3), 148.9 (C-5), 149.1 (C-6), 21.7 (6-CH$_3$), 21.5 (5-CH$_3$), 20.6 (3-CH$_3$).

Preparation Example 12

Synthesis of LQC-Y11 (Compound 11)

2-bromomethyl-3,5,6-trimethyl pyrazine 30 mmol prepared in example 1 and baicalein 1.48 mmol were put into a 25 ml three-necked flask and then DMF 9 ml and acetone 6 ml were added. Anhydrous kalium carbonate 0.5 g was added after the mixture was dissolved. The reaction liquid was agitated at 95° C. for 6.5 h under N$_2$ protection. The reaction was stopped when the raw materials were basically disappeared by the detection of TLC. Next, 5% sodium bicarbonate aqueous solution 30 ml was added into the reaction liquid and then the resultant reaction liquid was extracted by ethyl acetate 45 ml. All the extract was combined and evaporated to dryness. The residue was re-dissolved by a small amount of trichlormethane, silica gel 2.0 g was added thereinto, and the resultant sample was evaporated to dryness at a reduced pressure and was agitated. The obtained mixture was eluted with benzene:acetone=7:1 as the eluent to obtain a pale yellow powder 0.48 g. The yield was 60.0%, FAB-MS m/z 539 [M+H]$^+$ and the melting point was 227.8-229.0° C.; the hydrogen spectrum and carbon spectrum NMR data of compound 8 were as follows:

$^1$HNMR (500 MHZ, CDCl$_3$): 12.710 (s, 1H, 5-OH), 7.921~7.286 (m, 5H, aromatic hydrogen of the B ring), 6.841 (s, 1H, 8-H), 6.704 (s, 1H, 3-H), 5.281, 5.163 (s, 4H$_2$O—CH$_2$); 2.641-2.480 (s, 18H, pyrazine ring-CH$_3$);

$^{13}$CNMR (125 MHZ, CDCl$_3$): 182.7 (C-4), 164.0 (C-2), 92.2 (C-8), 105.7 (C-3), 106.6 (C-10), 126.3 (C-2', 6'), 129.2 (C-3', 5'), 131.3 (C-1), 131.5 (C-4'), 131.9 (C-6), 70.9 (7 position —CH$_2$—O ether), 74.1 (6 position —CH$_2$—O ether), 158.1 (C-7), 153.4 (C-9), 153.8 (C-5), δC of pyrazine ring: ether structure part at 7 position 151.8 (C-2), 146.4 (C-3), 148.7 (C-5), 150.3 (C-6), 21.8 (6-CH$_3$), 21.4 (5-CH$_3$), 20.7 (3-CH$_3$). ether structure part of 6 position, 150.7 (C-2), 144.4 (C-3), 148.6 (C-5), 150.2 (C-6), 21.6 (6-CH$_3$), 21.4 (5-CH$_3$), 20.3 (3-CH$_3$).

Effect Example 1

Observing the Effect of LQC-Y on the Tumor Angiogenesis Using CAM Method

1. Material
1.1 Animal

Embryonated chicken eggs of Lohmann of German, egg weight 50-60 g (Embryo experiment center of Chinese Agriculture University)

1.2 Experimental Medicine

LQC-Y (1-11) (self made respectively according to the preparation examples 2-12), wherein the purity was ≥98%, determined by high performance liquid chromatography (HPLC), meeting the requirements of the experiment. The powder was carefully sealed and preserved at 4° C.

2. Method 2.1 Preparation Method of the Sample to be Tested

Aseptic gelatin sponge, which was made into a wafer having a diameter of 5 mm by a hole-puncher in advance, was used as sample carrier. The prepared derivatives of bromotetramethylpyrazine series were added thereinto in an aseptic environment and different dosage groups were set according to the difference of the molecular weight of each medicine, including 10 μg/chicken embryo, 20 μg/chicken embryo and 40 μg/chicken embryo. The 0.9% physiological saline was used in a blank group. The samples were air-dried in an aseptic environment.

2.2 Egg Embryo Incubation and the Removing Method of Egg Embryo Air Sac

A hatching egg after disinfection was put into a 37° C. incubation box with air sac upward until the seventh day of incubation. The egg embryo was disinfected using alcohol at a super clean bench, and then a small hole was drilled at the top of the egg embryo using a dental drill, and the nearby egg shell and shell membrane were removed carefully to form a opening with the size of about 1.2 cm×1.2 cm. After spotting the location for applying the sample, the air sac was broken with injection needle at the interface between air sac and the yolk and then 1-2 drops of aseptic physiological saline was injected so that the air sac membrane was separated from CAM membrane. Then the upper air sac membrane was slightly removed with a nipper to expose the lower CAM membrane.

2.3 Sample Applying Method

The medicine-containing carrier was softly put by a nipper at the locations of CAM and yolk cyst membrane with fewer vessels, the opening was then sealed with aseptic transparent tape and incubation was continued for another 72 h.

2.4 Vessel Determination

After the incubation, the transparent tape blocking the chicken embryo air sac was softly removed with a nipper. The liquid of equal-volumetrically mixed methanol/acetone 1-2 ml was softly added and fixed at room temperature for 10 min. The CAM membrane was carefully removed and was put onto a slide. Then it was observed and a photograph was taken. The effect of the compounds on angiogenesis was evaluated by the count analytic method using the numbers of great vessels, medium vessels and small vessels arranged radially around the carrier.

2.5 Statistical Treatment

All the data were statistically analyzed using SPSS11.0 software pack. The difference between the administration group and the blank group was given through one-way variance analysis. $P<0.05$ had statistical significance.

3. Result

When respectively compared with the blank group about the amount of the small vessels, all the LQC-Y administration groups had a vessel growth inhibiting effect, wherein LQC-Y2 and LQC-Y8 had significant inhibiting effect and the results were shown as table 1, which showed that LQC-Y all had inhibiting effect on the growth of the new vessels.

TABLE 1 effect of LQC-Y on small vessel growth of CAM model ($\overline{X} \pm S$)

| Medicine No. | Blank group ($\overline{X} \pm S$) | Medicine group ($\overline{X} \pm S$) | Dosage (μg/chicken embryo) | Number of chicken embryo |
|---|---|---|---|---|
| LQC-Y1 | 10.3 ± 1.50 | 9.8 ± 2.14 | 40 | 20 |
| LQC-Y2 | 12.5 ± 2.59 | 4.3 ± 4.18** | 10 | 20 |
| LQC-Y2 | 12.5 ± 2.59 | 7.5 ± 3.40* | 40 | 20 |
| LQC-Y3 | 12.5 ± 2.59 | 12.0 ± 2.90 | 10 | 20 |
| LQC-Y3 | 12.5 ± 2.59 | 9.5 ± 4.55 | 40 | 20 |
| LQC-Y4 | 10.3 ± 1.50 | 9.5 ± 1.76 | 20 | 20 |
| LQC-Y5 | 8.67 ± 1.03 | 5.67 ± 1.21 | 20 | 20 |
| LQC-Y6 | 10.3 ± 1.50 | 7.3 ± 3.72 | 40 | 20 |
| LQC-Y7 | 12.0 ± 4.10 | 7.67 ± 4.32 | 40 | 20 |
| LQC-Y8 | 10.0 ± 2.19 | 3.83 ± 2.79** | 10 | 20 |
| LQC-Y8 | 10.0 ± 2.19 | 1.38 ± 1.22** | 40 | 20 |
| LQC-Y9 | 8.67 ± 1.03 | 7.67 ± 2.16 | 20 | 20 |
| LQC-Y10 | 12.5 ± 2.59 | 9.7 ± 3.98 | 10 | 20 |
| LQC-Y10 | 12.5 ± 2.59 | 10.8 ± 5.1 2 | 40 | 20 |
| LQC-Y11 | 10.3 ± 1.50 | 7.5 ± 3.89 | 20 | 20 |

Note:
compared with the blank group,
*$P < 0.05$,
**$P < 0.01$

4. Conclusion

LQC-Y (1-11) all had some effect on inhibiting the growth of the vessels wherein LQC-Y2 and LQC-Y8 had magnificent inhibiting effect.

Effect Example 2

Observing the Effect of LQC-Y on the Proliferation of Human Hepatoma Carcinoma Cells Bel7402 by MTT 1. Material
1.1 Tumor Strain Human hepatoma carcinoma cells Bel7402 were subcultured and preserved by immunity laboratory of the infectious disease research institute of PLA (People's Liberation Army).

1.2 Experimental Medicine

LQC-Y1, LQC-Y2, LQC-Y3, LQC-Y4, LQC-Y6, LQC-Y8, LQC-Y10 (self-prepared respectively according to the methods of above mentioned preparation examples), wherein the purity was ≥98%, determined by high performance liquid chromatography (HPLC), meeting the requirements of the experiment. The powder was carefully sealed and preserved at 4° C. and was dissolved by dimethyl sulfoxide to make a 1 ml/mg preserving liquid for use.

2. Method 2.1 Cell Culture

Human hepatoma carcinoma cells Bel7402 were recovered and subcultured using a culture flask. The preparation of the experiment was started when the cell growth entered into the exponential growth phase. The cells were then digested using pancreatic enzyme which had been filtrated at an increased pressure to prepare the cell suspension. After that the suspension was dyed for 3 min with 0.4% trypan blue. Then a blood cell counting plate was used to count the living cells which were not dyed and the dead cells which were dyed to blue. The number of the living cells identified by trypan blue was more than 98%.

2.2 Cell Proliferation Inhibiting Experiment

Three kinds of cells which were in the exponential growth phase were inoculated at the density of $1\times10^4$/ml, to a 96-well plate, 200 μl for each well. Then the plate was put in a 37° C. 5% $CO_2$ incubation box to be cultured for 24 h. The cultivation liquid was sucked away and 200 μl LQC-Y solutions of different concentrations were added thereinto (prepared with DMEM cultivation liquid containing 4% calf serum and the final concentration of which respectively were 10 μg, 20 μg, 40 μg), 4 parallel wells for each concentration. Supernatant cultivation liquid 100 μl was sucked away carefully from each well after being cultured for 24 h and 48 h, and MTS 20 μl was added into each well and homogeneously mixed. The resultant liquid was cultured in a 37° C. 5% $CO_2$ incubation box for a further 1 h. An enzyme-labeling quantitative instrument was used to measure the absorbance at 492 nm. The experiment was repeated for 3 times and then an inhibition ratio was calculated.

The inhibition ratio of cell proliferation (%)=[(average OD value of control group-average OD value of the administration group)/average OD value of control group]×100%

3. Result

LQC-Y (1, 2, 3, 4, 6, 8, 10) all showed an inhibiting effect on the proliferation of human hepatoma carcinoma cells Bel7402 which were cultured in vitro and the inhibiting effect had a dependence on dosage. The inhibiting effects of LQC-Y (1, 2, 3, 4, 8) were evident. When the concentrations were 40 μg/ml, the inhibition ratios of LQC-Y1, LQC-Y2, LQC-Y3, LQC-Y4, and LQC-Y8 on Bel7402 cells after functioning for 24 h, respectively were 86.44%, 66.98%, 99.16%, 86.44% and 94.43%, and as the concentration decreased, the inhibition ratio also decreased accordingly. The experiment results showed that LQC-Y1, LQC-Y2, LQC-Y3, LQC-Y4 and LQC-Y8 had evident inhibiting effect on the Bel7402 cells, wherein the effect of LQC-Y3 was best when the concentration was high. (Table 2)

tary Medical Sciences (certificate number: SCXK-(Jun) 2007-004). The sarcoma S180 cells of mice was kindly presented by the traditional Chinese medicine research institute of 320 Hospital. The ascites tumor bearing ascetic S180 mice were subcultured every 7 days.

1.2 Experiment Medicine

LQC-Y2 (self-prepared), wherein the purity was ≥98%, determined by high performance liquid chromatography (HPLC), meeting the requirements of the experiment. The oily substance was carefully sealed and preserved at 4° C.

Cyclophosphamide for injection: Shanxi Powerdone Pharmaceutics Co., Ltd.

2. Method 2.1 The Establishing of the Animal Model

The S180 mice that had been inoculated for 7 days were killed by breaking the neck thereof and ascites was taken from the mice respectively in an aseptic environment and the ascites was washed using RPMI1640 culture medium for 2 times and then made into a $2\times10^7$/ml cell suspension using aseptic physiological saline. Then the obtained S180 cell suspension was inoculated hypodermically at the right axillary of mice, 0.1 ml for each mouse and 50 mice total, to establish the solid tumor model.

2.2 Experiment Grouping 60 mice were divided into 2 categories, including 6 groups, according to the random number table method, i.e. normal control group of the first category, and S180 solid tumor groups of the second category which included positive (cyclophosphamide) control group, negative control group, small dosage group, middle dosage group and large dosage group, 10 mice for each group. The experiment was repeated for 3 times.

2.3 Administration Method

LQC-Y2 was made into an emulsion using corn oil. The dosage of the small dosage group was 75 mg/Kg, the dosage of the middle dosage group was 150 mg/Kg, and the dosage of the large dosage group was 300 mg/kg. Equal volume of corn oil was injected into the mice of the negative control group, cyclophosphamide injection 0.02 g/(Kg.d) was injected into the mice of the positive control group. These medicines were

TABLE 2 inhibiting effect of LQC-Y on the proliferation of Bel7402 cell strains

| concentration (μg/ml) | 24 h inhibition ratio (%) | | | | | | |
|---|---|---|---|---|---|---|---|
| | LQC-Y1 | LQC-Y2 | LQC-Y3 | LQC-Y4 | LQC-Y6 | LQC-Y8 | LQC-Y10 |
| 10 | 67.39% | 20.09% | 34.53% | 39.31% | 26.75% | 39.31% | — |
| 20 | 76.66% | 61.2% | 89.07% | 44.58% | 67.23% | 44.58% | 7.82% |
| 40 | 86.44% | 66.98% | 99.16% | 94.42% | 81.21% | 54.07% | 5.69% |

4. Conclusion

LQC-Y1, LQC-Y2, LQC-Y3, LQC-Y4 and LQC-Y8 had evident inhibiting effect on the Bel7402 cells, wherein the effect of LQC-Y3 was best when the concentration was high and its inhibition ratio reached 99.16%.

Effect Example 3

Tumor Inhibiting Effect of LQC-Y2 of Tumor Bearing S180 Mice

1. Material 1.1 Experimental Animals and Tumor Strain

Healthy female Balb/C mice: weight being 18-22 g, purchased from Laboratory Animal Center of Academy of Miliadministrated 0.1 ml per mouse by intraperitoneal injection every the other day continuously for 15 days. During this period, the common behavior, hair and excrement and so on were observed daily. The mice that had been inoculated with S180 by hypodermic inoculation were killed by breaking the necks thereof after 24 h after the last administration and the tumor, liver and spleen were then taken.

2.4 Calculation of Spleen Index and Liver Index

The weight of the solid tumor group mice were measured after all the administration was over and then the mice were killed. The spleens and the livers thereof were weighed by an electronic balance. The spleen index was calculated as the spleen weight of a mouse (mg)/the body weight of a mouse(g) and the liver index was calculated as the liver weight of a mouse(100 g)/the body weight of a mouse(g).

2.5 Calculation of the Tumor Inhibiting Ratio

The solid tumor negative control group mice were weighed on the next day after the administration was finished (the eyeballs of the mice were removed to bleed and the serum was collected for subsequent experimental use). Then the mice were killed by breaking the neck thereof. The tumor tissues were taken out and weighed by an electronic balance to calculate the tumor-inhibiting ratio.

$$\text{Inhibiting ratio (\%)} = \frac{\text{Average tumor weight of the negative control group} - \text{average tumor weight of the administration group}}{\text{Average tumor weight of the control group}} \times 100\%$$

2.6 Statistical Treatment

All the data were statistically analyzed using SPSS11.0 software pack. The comparison of the enumeration data was carried out with $X^2$ test. P<0.05 had statistical significance.

3. Experiment Result 3.1 Anti-Cancer Activity of LQC-Y2 in Vivo

The LQC-Y2 had no effect on the growth of the S180 sarcoma mice's weight while the weight growth of the positive control group is relatively low. The tumor growth inhibiting ratio of the small, middle and large dosage group of the tumor-bearing S180 sarcoma mice were respectively 6.87%, 35.88% and 29.15%. (Table 3)

TABLE 3

Inhibiting effect of LQC-Y2 on S180 sarcoma of mice (x ± s)

| Group | Weight growth (g) | Tumor weight (g) | Tumor inhibiting ratio (%) |
|---|---|---|---|
| Blank control group | — | — | — |
| Model group | 9.57 ± 2.15 | 1.31 ± 0.40 | — |
| Cyclophosphamide group | 8.98 ± 3.80①③ | 0.15 ± 0.13④ | 88.55% |
| Small dosage group | 6.43 ± 3.79 | 1.22 ± 0.62 | 6.87% |
| Middle dosage group | 3.78 ± 3.38 | 0.84 ± 0.53 | 35.88% |
| Large dosage group | 4.89 ± 1.61 | 0.92 ± 0.49 | 29.15% |

Note:
1. Compared with the normal control group: ①P < 0.05, ②P < 0.01
2. Compared with the negative control group: ③P < 0.05, ④P < 0.01

3.2 Change of the Liver Index and Spleen Index of Mice of Each Group

As shown in Table 3-2, the liver index and the spleen index and so on of the S180 mice of cyclophosphamide group were all smaller than those of the negative control group, and had statistical significance. The mice spleen index of the small dosage group of the LQC-Y2 was bigger than the negative control group and therefore had significant difference, while the live index showed no difference. (Table 4).

TABLE 4

Effect of LQC-Y2 on spleen index and liver index of S180 mice (x ± s)

| Group | Spleen index (100 g/g) | Spleen index (mg/g) |
|---|---|---|
| Blank control group | 5.01 ± 0.46 | 4.10 ± 0.77 |
| Model group | 5.34 ± 0.50 | 4.10 ± 1.24 |
| Cyclophosphamide group | 5.29 ± 0.47①④ | 2.91 ± 0.10①④ |
| Small dosage | 5.15 ± 0.50 | 5.13 ± 1.24①③ |

TABLE 4-continued

Effect of LQC-Y2 on spleen index and liver index of S180 mice (x ± s)

| Group | Spleen index (100 g/g) | Spleen index (mg/g) |
|---|---|---|
| Middle dosage | 4.79 ± 0.28 | 3.69 ± 0.47 |
| Large dosage | 4.95 ± 0.39 | 4.18 ± 57 |

Note:
1. Compared with the normal control group: ①P < 0.05, ②P < 0.01
2. Compared with the negative control group: ③P < 0.05, ④P < 0.01

4. Result 4.1 LQC-Y2 had Some Effect on Inhibiting the Growth of the Sarcoma of the S180 Mice.

4.2 LQC-Y2 can Increase the Spleen Index of the Tumor Bearing Mice.

Effect Example 4

Tumor Inhibiting Effect of LQC-Y3 on Tumor Bearing S180 Mice

1. Material 1.1 Experimental Animals and Tumor Strain

Healthy female Balb/C mice: weight being 18-22 g, purchased from Laboratory Animal Center of Academy of Military Medical Sciences (certificate number: SCXK-(Jun) 2007-004). The sarcoma S180 cells of mice: kindly presented by the traditional Chinese medicine research institute of 320 Hospital. The ascites tumor bearing S180 mice were subcultured every 7 days.

1.2 Experiment Medicine

LQC-Y3 (self-prepared), wherein the purity was ≥98%, determined by high performance liquid chromatography (HPLC), meeting the requirements of the experiment. The powder was carefully sealed and preserved at 4° C.

Cyclophosphamide for injection: Shanxi Powerdone Pharmaceutics Co., Ltd.

2. Method 2.1 The Establishing of the Animal Model

The S180 mice that had been inoculated for 7 days were killed by breaking the neck thereof and ascites was taken from the mice respectively in an aseptic environment and the ascites was washed using RPMI1640 culture medium for 2 times and then made into a 2×10$^7$/ml cell suspension using aseptic physiological saline. Then the obtained S180 cell suspension was inoculated hypodermically at the right axillary of mice, 0.1 ml for each mouse and 50 mice total, to establish the solid tumor model.

2.2 Experiment Grouping 60 mice were divided into 2 categories, including 6 groups, according to the random number table method, i.e. normal control group of the first category, and S180 solid tumor groups of the second category which included positive (cyclophosphamide) control group, negative control group, small dosage group, middle dosage group and large dosage group, 10 mice for each group. The experiment was repeated for 3 times.

2.3 Administration Method

LQC-Y3 was prepared using 0.5% CMC-Na. The dosage of the small dosage group was 75 mg/Kg, the dosage of the middle dosage group was 150 mg/Kg, and the dosage of the large dosage group was 300 mg/kg. Equal volume of 0.5% CMC-Na was injected into the mice of the negative control group and cyclophosphamide injection 0.02 g/(Kg.d) was injected into the mice of the positive control group. These medicines were administered 0.1 ml per mouse by intraperitoneal injection every the other day continuously for 15 days. During this period, the common behavior, hair, excrement and so on were observed daily. The mice that had been inoculated with S180 by hypodermic inoculation were killed by breaking the neck thereof after 24 h after the last administration and the tumor, liver and spleen were then taken.

2.4 Calculation of Spleen Index and Liver Index

The weight of the solid tumor group mice were measured after all the administration was finished and then the mice were killed. The spleens and the livers thereof were weighed by an electronic balance. The spleen index was calculated as the spleen weight of a mouse (mg)/the body weight of a mouse (g) and the liver index was calculated as the liver weight of a mouse (100 g)/the body weight of a mouse (g).

2.5 Calculation of the Tumor Inhibiting Ratio

The solid tumor negative control group mice were weighed on the next day after the administration was finished (the eyeballs of the mice were removed to bleed and the serum was collected for subsequent experimental use). Then the mice were killed by breaking the neck thereof. The tumor tissues were taken out and weighed by an electronic balance to calculate the tumor inhibiting ratio.

Inhibiting ratio (%) =

$$\frac{\text{Average tumor weight of the negative control group} - \text{average tumor weight of the administration group}}{\text{Average tumor weight of the control group}} \times 100\%$$

2.6 Statistical Treatment

All the data were statistically analyzed using SPSS11.0 software pack. The comparison of the enumeration data was carried out with $X^2$ test. $P<0.05$ had statistical significance.

3. Experiment Result 3.1 Anti-Cancer Activity of LQC-Y3 in Vivo

The LQC-Y3 had no effect on the growth of the S180 sarcoma mice's weight while the weight growth of the positive control group was relatively low. The tumor growth inhibiting ratio of the small, middle and large dosage group of the tumor-bearing S180 sarcoma mice were respectively 33.98%, 37.23% and 50.00%. And the large dosage group had statistical significance compared with negative control group (Table 5).

TABLE 5

Inhibiting effect of LQC-Y3 on S180 sarcoma of mice (x ± s)

| Group | Weight growth (g) | Tumor weight (g) | Tumor inhibiting ratio (%) |
| --- | --- | --- | --- |
| Blank control group | 7.23 ± 2.16 | — | — |
| Model group | 9.57 ± 2.15 | 0.94 ± 0.41 | — |
| Cyclophosphamide group | 6.90 ± 2.04①③ | 0.25 ± 0.16④ | 73.40% |
| Small dosage | 10.15 ± 2.81① | 0.63 ± 0.30 | 33.98% |
| Middle dosage | 7.54 ± 3.56 | 0.59 ± 0.28 | 37.23% |
| Large dosage | 7.72 ± 3.68 | 0.47 ± 0.23③ | 50.0% |

Note:
1. Compared with the normal control group: ①$P < 0.05$, ②$P < 0.01$
2. Compared with the negative control group: ③$P < 0.05$, ④$P < 0.01$ 3.2 Change of the Liver Index and Spleen Index of Mice of Each Group As shown in Table 3-2, the liver index and the spleen index and so on of the cyclophosphamide group were all smaller than those of the negative control group, and had statistical significance. The mice spleen indexes of the middle and large dosage group of the LQC-Y3 were bigger than the negative control group, has significant difference, while the liver index shows no difference. (Table 6).

TABLE 6 effect of LQC-Y 3 on spleen index and liver index of S180 mice (x ± s)

| group | Liver index (100 g/g) | Spleen index (mg/g) |
| --- | --- | --- |
| blank control group | 5.01 ± 0.46 | 4.10 ± 0.77 |
| Model control group | 5.28 ± 0.48 | 4.33 ± 0.84 |
| Cyclophosphamide | 5.19 ± 0.33 | 3.93 ± 1.11①④ |
| Small dosage group | 5.43 ± 0.59 | 4.36 ± 1.13 |
| Middle dosage group | 5.39 ± 0.46 | 5.68 ± 1.77①④ |
| Large dosage group | 5.45 ± 0.72 | 4.82 ± 2.23② |

Note:
1. Compared with normal control group: ①$P < 0.05$, ②$P < 0.01$
2. Compared with the negative control group: ③$P < 0.05$, ④$P < 0.01$ 4. Conclusion 4.1 LQC-Y3 can Notably Inhibit the Growth of the S180 Mice Sarcoma.

4.2 LQC-Y3 can Increase the Spleen Index of the Tumor Bearing Mice.

TOXICITY EXAMPLE

Toxicity Example 1

1. Experimental Project: Acute Toxic Experiment of Mice by Oral Administration

2. Experimental Material:

ICR white mice (half female and half male, 18-22 g, experiment animal certificate No.: SCXK (Jing) 2006-0009);

LQC-Y3 (white powder (self prepared); and LQC-Y3 5000 mg was dissolved into 0.5% sodium carboxymethyl cellulose 100 ml and then suspended by supersonic wave. The suspension was used in situ).

3. Experimental Method:

The qualified animals were quarantined and weighed before the administration. Then the animals were divided into groups randomly by weight. The intragastric administration tool for mice was used to carry out the intragastric administration. The mice were fasted but not water-deprived (continuously for 14 h) overnight before being administrated. The mice were administrated at 9:00 AM for the first time (2000 mg/kg) on the present administration day and observed continuously for 1 h. The mice were administrated for the second time (2000 mg/kg) at an interval of 6 h since the first administration and observed continuously for 1 h. The mice were administered for the third time (2000 mg/kg) at an interval of 6 h since the second administration, observed continuously for 1 h and then the mice were fed.

4. Experiment Results:

No death was observed in 12 h after the administration. The death condition of each group mice in 14 days was shown as the following table.

TABLE 7 summary of the routine observation results of the mice
acute toxic experiment of LQC-Y3 by oral administration

| Group | sex | Animal Number | Animal reaction in 14 days after the administration | | | | | | |
|---|---|---|---|---|---|---|---|---|---|
| | | | Appearance | Behavior | Hair | Respiration | Posture | Reaction | Death |
| Control group | ♂ | 10 | ✓ | ✓ | ✓ | ✓ | ✓ | ✓ | 0 |
| | ♀ | 10 | ✓ | ✓ | ✓ | ✓ | ✓ | ✓ | 0 |
| LQC-Y3 | ♂ | 10 | ✓ | ✓ | ✓ | ✓ | ✓ | ✓ | 0 |
| | ♀ | 10 | ✓ | ✓ | ✓ | ✓ | ✓ | ✓ | 0 |

Note:
✓ means normal.

5. Summary

In the present mouse acute toxic experiment of LQC-Y3 by oral administration, the maximum dosage of 6000 mg/kg was administered to the mice and observed continuously for 14 days. No toxic reaction was observed, which meant that the safety of this medicine was high.

FORMULATION EXAMPLE

Formulation Example 1

LQC-Y3 10 g was taken and then proper injection (including freeze-dry powder injection and aseptic packaging dry powder injection) excipients (distilled water, polyethylene glycol) were added thereinto. An antitumor injection was prepared according to the common injection (including freeze-dry powder injection and aseptic packaging dry powder injection) preparing technology.

Formulation Example 2

LQC-Y3 10 g was taken and then proper tablet (including extended action tablet, matrix tablet, coated tablet, dispersible tablet, etc.) excipients (starch, sodium carboxymethylcellulose) were added thereinto. An antitumor tablet was prepared according to the common tablet (including extended action tablet, matrix tablet, coated tablet, dispersible tablet, etc.) preparing technology.

Formulation Example 3

LQC-Y3 10 g was taken and proper capsule excipients (starch, microcrystalline cellulose) were added thereinto. An antitumor capsule was prepared according to the common capsule preparing technology.

Formulation Example 4

LQC-Y3 10 g was taken and proper emulsion (including micro emulsion, nano emulsion, etc.) excipients (polylactic acid) were added thereinto. An antitumor emulsion (including micro emulsion, nano emulsion, etc.) was prepared according to the common emulsion preparing technology.

Formulation Example 5

LQC-Y3 10 g was taken and proper granule excipients (sodium carboxymethylcellulose, microcrystalline cellulose) were added thereinto. An antitumor granule was prepared according to the common granule preparing technology.

Formulation Example 6

LQC-Y3 10 g was taken and proper sustained release formulation excipients (sodium carboxmethylcellulose, microcrystalline cellulose) were added thereinto. An antitumor sustained release formulation was prepared according to the common sustained release formulation preparing technology.

Formulation Example 7

LQC-Y3 10 g was taken and proper oral liquid excipients (distilled water, sucrose) were added thereinto. An antitumor oral liquid was prepared according to the common oral liquid preparing technology.

Formulation Example 8

LQC-Y3 10 g was taken and proper liposome formulation excipients (lecithin, cephalin) were added thereinto. An antitumor liposome formulation was prepared according to the common liposome formulation preparing technology.

Formulation Example 9

LQC-Y 10 g was taken and proper injection (including freeze-dry powder injection and aseptic packaging dry powder injection) excipients were added thereinto. An antitumor injection was prepared according to the injection preparing technology.

Formulation Example 10

LQC-Y 10 g was taken and proper tablet (including extended action tablet, matrix tablet, coated tablet, dispersible tablet, etc.) excipients were added thereinto. An antitumor tablet was prepared according to the tablet (including extended action tablet, matrix tablet, coated tablet, dispersible tablet, etc.) preparing technology.

Formulation Example 11

LQC-Y 10 g was taken and proper capsule excipients were added thereinto. An antitumor capsule was prepared according to the capsule preparing technology.

Formulation Example 12

LQC-Y 10 g was taken and proper emulsion (including micro emulsion, nano emulsion, etc.) excipients were added thereinto. An antitumor emulsion (including micro emulsion, nano emulsion, etc.) was prepared according to the emulsion preparing technology.

Formulation Example 13

LQC-Y 10 g was taken and proper granule excipients were added thereinto. An antitumor granule was prepared according to the granule preparing technology.

Formulation Example 14

LQC-Y 10 g was taken and proper sustained release formulation excipients were added thereinto. An antitumor sustained release formulation was prepared according to the sustained release formulation preparing technology.

Formulation Example 15

LQC-Y 10 g was taken and proper oral liquid excipients were added thereinto. An antitumor oral liquid was prepared according to the oral liquid preparing technology.

Formulation Example 16

LQC-Y 10 g was taken and proper liposome formulation excipients were added thereinto. An antitumor liposome formulation was prepared according to the liposome formulation preparing technology.

What is claimed:
1. A compound of formula 1 or the pharmaceutically acceptable salt thereof:

formula 1 wherein the compound of formula 1 is an ester of R-acid with trimethyl pyrazine methanol, and the R-acid is selected from the group consisting of oleanolic acid, glycyrrhetinic acid or pachymic acid.

2. The method for synthesizing the compound according to claim 1, comprising the following steps:

wherein R is as defined in formula 1;
step 1: reacting compound 5 with NBS (N-bromosuccimide) to obtain compound 6; and
step: reacting compound 6 with hydroxyl or carbonyl compound containing R to obtain compound 1.

3. The method according to claim 2, wherein step (1) is carried out in a solvent selected from tetrachloromethane, acetonitrile and dioxane.

4. The method according to claim 2, wherein step (1) includes adding a radical initiator.

5. The method according to claim 2, wherein step (1) is carried out with illumination from an incandescent lamp.

6. The method according to claim 2, wherein step (2) is carried out in a solvent selected from xylene, acetone and N,N-dimethyl formamide.

7. The method according to claim 2, wherein the reaction in step (2) is carried out in the presence of with a substance selected from triethylamine, kalium carbonate and piperidine.

8. The method according to claim 2, wherein step (2) is carried out under heating.

9. The method of making a compound according to claim 1, comprising dissolving oleanolic acid into an organic solvent to react with bromotetramethylpyrazine in the presence of a catalyst to generate compound 3 (LQC-Y3) of the formula:

10. The method of making a compound according to claim 1, comprising dissolving glycyrrhetinic acid into an organic solvent to react with bromotetramethylpyrazine in the presence of a catalyst to generate compound 4 (LQC-Y4) of the formula:

* * * * *